(12) United States Patent
Ozadali et al.

(10) Patent No.: US 9,612,184 B2
(45) Date of Patent: Apr. 4, 2017

(54) MIXER SENSORS AND METHODS FOR USING SAME

(75) Inventors: Ferhan Ozadali, Muskegon, MI (US); Dharmendra Kumar Mishra, Fremont, MI (US); Rabiha Sulaiman, Klang (MY)

(73) Assignee: Nestec S.A., Vevey (CH)

( * ) Notice: Subject to any disclaimer, the term of this patent is extended or adjusted under 35 U.S.C. 154(b) by 725 days.

(21) Appl. No.: 14/111,809

(22) PCT Filed: May 1, 2012

(86) PCT No.: PCT/EP2012/057954
§ 371 (c)(1),
(2), (4) Date: Oct. 15, 2013

(87) PCT Pub. No.: WO2012/152616
PCT Pub. Date: Nov. 15, 2012

(65) Prior Publication Data
US 2014/0033803 A1 Feb. 6, 2014

Related U.S. Application Data

(60) Provisional application No. 61/483,092, filed on May 6, 2011.

(51) Int. Cl.
*G01N 11/14* (2006.01)
*B01F 7/00* (2006.01)

(52) U.S. Cl.
CPC .......... *G01N 11/14* (2013.01); *B01F 7/00033* (2013.01); *B01F 7/00133* (2013.01);
(Continued)

(58) Field of Classification Search
CPC . G01N 11/14; B01F 7/00133; B01F 7/00033; B01F 7/00141; B01F 7/00175;
(Continued)

(56) References Cited

U.S. PATENT DOCUMENTS

| 4,013,234 A | 3/1977 | Rudolph |
| 2005/0132782 A1* | 6/2005 | Wallevik ................. B01F 7/063 73/54.28 |

(Continued)

FOREIGN PATENT DOCUMENTS

GB 1217329 12/1970

OTHER PUBLICATIONS

International Search Report and Written Opinion dated Aug. 23, 2012, received in PCT Application No. PCT/EP2012/057954.

*Primary Examiner* — Michael A Lyons
*Assistant Examiner* — Suman K Nath
(74) *Attorney, Agent, or Firm* — Gary M. Lobel, Esq.

(57) ABSTRACT

Apparatuses for measuring rheological properties of fluids and methods for using same are provided. In a general embodiment, the present disclosure provides a mixer sensor that is configured to be attached to a rheometer drive head and used to measure rheological properties of a fluid having particulates over a wide range of temperatures and shear rates. Apparatuses capable of obtaining rheological data of a fluid having particulates over a wide range of temperatures and shear rates provides for more precise rheological measurements. The temperatures may be very high temperatures that exceed 100° C., and the shear rates may includes a range of shear rates that are typically found in a processing pipeline system.

40 Claims, 5 Drawing Sheets

(52) U.S. Cl.
CPC ...... *B01F 7/00141* (2013.01); *B01F 7/00175* (2013.01); *B01F 7/00291* (2013.01); *B01F 7/00425* (2013.01); *B01F 2215/0422* (2013.01); *B01F 2215/0431* (2013.01)

(58) Field of Classification Search
CPC .............. B01F 7/00425; B01F 7/00291; B01F 2215/0422; B01F 2215/0431
USPC ........... 73/54.01, 54.23, 54.32, 54.33, 54.35, 73/54.38
See application file for complete search history.

(56) References Cited

U.S. PATENT DOCUMENTS

| | | | |
|---|---|---|---|
| 2006/0249432 A1* | 11/2006 | Bourke | B01F 3/04531 209/169 |
| 2008/0060423 A1* | 3/2008 | Jau | G01N 11/14 73/54.31 |
| 2009/0107196 A1* | 4/2009 | Jung | B01F 7/00116 71/59 |
| 2010/0010675 A1 | 1/2010 | Anderberg | |
| 2011/0083474 A1* | 4/2011 | Berndhaeuser | B01F 7/00125 65/135.4 |
| 2012/0282688 A1* | 11/2012 | Knight | B01J 19/0066 435/325 |

\* cited by examiner

MIXER SENSORS AND METHODS FOR USING SAME

BACKGROUND

The present disclosure generally relates to apparatuses for characterizing rheological properties of materials and methods for using same. More specifically, the present disclosure is directed to mixer sensors for rheological characterization of fluids having particles at various processing conditions.

Different types of rheological testing equipment have been widely available for use in laboratories, manufacturing plants, etc. for testing rheological characteristics of materials. Although apparatuses for testing rheological properties of materials are readily available in the art, they cannot always be used with every fluid requiring rheological characterization. For example, known apparatuses may not be suitable for use in characterizing fluids exposed to high temperature environments, such as aseptic processing systems. Additionally, known apparatuses may not be suitable for use with fluids having particulates. Indeed, most commercially available apparatuses require any particulates in a fluid to be strained, or otherwise removed, prior to rheological characterization. In this manner, the only portion of the sample left for characterization is the fluid portion, which may give a less accurate rheological measurement of the sample that may not reflect the actual processing conditions of the sample within the processing pipeline system.

SUMMARY

The present disclosure provides apparatuses for use with measuring rheological properties of a material and methods for using same. In a general embodiment, an apparatus for measuring rheological properties of a material is provided. The apparatus includes a shaft comprising at least three blades arranged in an interrupted helical shape and a base configured to receive an end of the shaft.

In an embodiment, the shaft has a length from about 2 inches to about 6 inches. The shaft may also be about 4 inches long. The shaft may be manufactured from a material selected from the group consisting of steel, steel alloys, stainless steel, chromium, cobalt-chromium, or combinations thereof. In an embodiment, the material is cobalt-chromium.

In an embodiment, the base is configured to receive a bottom end of the shaft. The base may further include at least one o-ring groove configured to accept an o-ring seal. In an embodiment, the base is manufactured from a material selected from the group consisting of steel, steel alloys, stainless steel, chromium, cobalt-chromium, or combinations thereof. In an embodiment, the material is cobalt-chromium.

In an embodiment, the apparatus includes a drive head attachment. The drive head attachment is so constructed and arranged to attach to one of a rheometer and a viscometer. The drive head attachment may be configured to receive a top end of the shaft therein. The drive head attachment may be manufactured from a material selected from the group consisting of steel, steel alloys, stainless steel, chromium, cobalt-chromium, or combinations thereof. In an embodiment, the material is cobalt-chromium.

In an embodiment, the plurality of blades are radially spaced about an axis of the shaft. The plurality of blades may be radially spaced from each other by about 45° to about 135°. In an embodiment, the plurality of blades are radially spaced from each other by about 90° about an axis of the shaft and along a circumference of the shaft.

In an embodiment, the plurality of blades are vertically spaced from each other by about 0.25 inches to about 1.25 inches. The plurality of blades may also be vertically spaced from each other by about 0.75 inches. In an embodiment, the plurality of blades are radially spaced from each other by about 90° and vertically spaced from each other by about 0.75 inches.

In an embodiment, each of the plurality of blades is rotated about 20° to about 80° from horizontal. Each of the plurality of blades may also be rotated about 45° from horizontal.

In an embodiment, each of the plurality of blades is substantially triangularly shaped.

In an embodiment, the base is further configured to mate with a particle screen. The particle screen may include an open center portion that is configured to receive the base. The particle screen may be substantially circular in shape and may include a plurality of holes between the center portion and the circumference. The particle screen may have a diameter from about 1 to about 3 inches. In an embodiment, the particle screen comprises a diameter of about 1.5 inches. The particle screen may also rest on a plurality of pegs that are formed integrally with particle screen or are friction fit into the holes of particle screen.

In an embodiment, the apparatus includes a temperature probe. The temperature probe may be configured to extend through at least one of the holes of the particle screen.

In another embodiment, an apparatus for measuring rheological properties of a material is provided. The apparatus includes a shaft, at least two curved blades attached to the shaft, each curved blade comprising three sections, and at least two linear blades attached to the shaft.

In an embodiment, the shaft has a length from about 2 inches to about 6 inches. The shaft may also be about 4 inches long. The shaft may be manufactured from a material selected from the group consisting of steel, steel alloys, stainless steel, chromium, cobalt-chromium, or combinations thereof. In an embodiment, the material is cobalt-chromium.

In an embodiment, the base is configured to receive a bottom end of the shaft. The base may further include at least one o-ring groove configured to accept an o-ring seal. In an embodiment, the base is manufactured from a material selected from the group consisting of steel, steel alloys, stainless steel, chromium, cobalt-chromium, or combinations thereof. In an embodiment, the material is cobalt-chromium.

In an embodiment, the apparatus includes a drive head attachment. The drive head attachment is so constructed and arranged to attach to one of a rheometer and a viscometer. The drive head attachment may be configured to receive a top end of the shaft therein. The drive head attachment may be manufactured from a material selected from the group consisting of steel, steel alloys, stainless steel, chromium, cobalt-chromium, or combinations thereof. In an embodiment, the material is cobalt-chromium.

In an embodiment, the base is further configured to mate with a particle screen. The particle screen may include an open center portion that is configured to receive the base. The particle screen may be substantially circular in shape and may include a plurality of holes between the center portion and the circumference. The particle screen may have a diameter from about 1 to about 3 inches. In an embodiment, the particle screen comprises a diameter of about 1.5 inches. The particle screen may also rest on a plurality of pegs that are formed integrally with particle screen or are friction fit into the holes of particle screen.

In an embodiment, the apparatus includes a temperature probe. The temperature probe may be configured to extend through at least one of the holes of the particle screen. In an embodiment, each of the curved blades has a total length from about 1 inch to about 4 inches.

In an embodiment, each of the curved blades has a total length of about 2.7 inches. Each of the three sections may also be separated by a space. Each of the three sections may be equal in length. Each curved blade may occupy an angular space from about 30° to about 80°. In an embodiment, each curved blade occupies an angular space that is about 75°. The at least two curved blades may be radially spaced from each other by about 180° about an axis of the shaft.

In an embodiment, the linear blades are surface scraper blades. Each of the linear blades may be attached to the shaft at a top end and a bottom end of the linear blade. Each of the linear blades has a length from about 1.5 inches to about 3.5 inches. In an embodiment, each of the linear blades has a length that is about 2.3 inches. The linear blades may have a step-like shape forming two different parallel portions of the linear blade. A first parallel portion of the linear blade may have a length from about 0.1 to about 0.2 inches. In an embodiment, the first parallel portion of the linear blade has a length of about 0.15 inches. The second parallel portion of the linear blade has a length from about 0.2 inches to about 0.6 inches. In an embodiment, the second parallel portion of the linear blade has a length of about 0.4 inches. The at least two linear blades may be radially spaced from each other by about 180° about an axis of the shaft.

In yet another embodiment, an apparatus for measuring rheological properties of a material is provided. The apparatus includes a shaft comprising first and second pairs of blades and an inverted cone, wherein each of the first pair of blades are oriented substantially vertically, and wherein each of the second pair of blades are oriented at an acute angle with respect to a horizontal plane.

In an embodiment, the shaft has a length from about 2 inches to about 6 inches. The shaft may also be about 4 inches long. The shaft may be manufactured from a material selected from the group consisting of steel, steel alloys, stainless steel, chromium, cobalt-chromium, or combinations thereof. In an embodiment, the material is cobalt-chromium.

In an embodiment, the base is configured to receive a bottom end of the shaft. The base may further include at least one o-ring groove configured to accept an o-ring seal. In an embodiment, the base is manufactured from a material selected from the group consisting of steel, steel alloys, stainless steel, chromium, cobalt-chromium, or combinations thereof. In an embodiment, the material is cobalt-chromium.

In an embodiment, the apparatus includes a drive head attachment. The drive head attachment is so constructed and arranged to attach to one of a rheometer and a viscometer. The drive head attachment may be configured to receive a top end of the shaft therein. The drive head attachment may be manufactured from a material selected from the group consisting of steel, steel alloys, stainless steel, chromium, cobalt-chromium, or combinations thereof. In an embodiment, the material is cobalt-chromium.

In an embodiment, the base is further configured to mate with a particle screen. The particle screen may include an open center portion that is configured to receive the base. The particle screen may be substantially circular in shape and may include a plurality of holes between the center portion and the circumference. The particle screen may have a diameter from about 1 to about 3 inches. In an embodiment, the particle screen comprises a diameter of about 1.5 inches. The particle screen may also rest on a plurality of pegs that are formed integrally with particle screen or are friction fit into the holes of particle screen.

In an embodiment, the apparatus includes a temperature probe. The temperature probe may be configured to extend through at least one of the holes of the particle screen. In an embodiment, each of the curved blades has a total length from about 1 inch to about 4 inches.

In an embodiment, the first pair of blades are radially spaced about an axis of the shaft. The first pair of blades may be radially spaced from each other by about 180°. The first pair of blades are vertically spaced from each other such that a bottom side of a first blade is at the same vertical height as a top side of a second blade. The first pair of blades are radially spaced from each other by about 180° and vertically spaced from each other such that a bottom side of a first blade is at the same vertical height as a top side of a second blade. The first pair of blades comprise a shape selected from the group consisting of rectangle, square, or combinations thereof. Each of the first pair of blades may have a width from about 10 to 15 mm. In an embodiment, each of the first pair of blades has a width of about 13 mm. Each of the first pair of blades may have a height from about 10 to 20 mm. In an embodiment, each of the first pair of blades has a height of about 15 mm. In an embodiment, the first pair of blades are located at a bottom portion of the shaft.

In an embodiment, the second pair of blades are radially spaced about an axis of the shaft. The second pair of blades may be radially spaced from each other by about 180°. The second pair of blades may be located in substantially the same horizontal plane. In an embodiment, the second pair of blades are radially spaced from each other by about 180° and located in substantially the same horizontal plane. Each of the second pair of blades may be rotated about 15° from vertical. In an embodiment, each of the second pair of blades is rotated about 45° from horizontal. Each of the second pair of blades includes a shape selected from the group consisting of rectangle, square, or combinations thereof. Each of the second pair of blades may have a height from about 10 to about 20 mm. In an embodiment, each of the second pair of blades has a height of about 15 mm. Each of the second pair of blades may have a width from about 10 mm to about 15 mm. In an embodiment, each of the second pair of blades has a width of about 13.5 mm. In an embodiment, the second pair of blades are located at a middle portion of the shaft.

In an embodiment, the first pair of blades is separated from the second pair of blades along the shaft by a distance from about 5 mm to about 15 mm. The first pair of blades may also be separated from the second pair of blades along the shaft by a distance of about 10 mm.

A base of the cone has a diameter from about 20 mm to about 40 mm.

In an embodiment, a base of the cone may have a diameter of about 30 mm. In an embodiment, the cone forms an angle with the shaft from about 15° to about 45°. The cone may form an angle with the shaft of about 30° or 31°. In an embodiment, the inverted cone is located at a top portion of the shaft.

In still yet another embodiment, a system for measuring rheological properties of a material is provided. The system includes a device comprising a stationary measurement cup and an impeller drive head and an impeller attached to the impeller drive head. The impeller includes a shaft comprising at least three blades arranged in an interrupted helical shape and a base configured to receive an end of the shaft.

In an embodiment, the device is one of a rheometer and a viscometer.

In an embodiment, the system includes a fluid contained within the measurement cup. The fluid may include particulates.

In an embodiment, the stationary measurement cup includes a stationary particle screen at a bottom of the cup. The stationary measurement cup may also include an integral temperature probe. In an embodiment, the temperature probe is configured to mate with the particle screen.

In another embodiment, a system for measuring rheological properties of a material is provided. The system includes a device comprising a stationary measurement cup and an impeller drive head, and an impeller attached to the impeller drive head. The impeller includes a shaft, at least two curved blades attached to the shaft, each curved blade comprising three sections, and at least two linear blades attached to the shaft.

In an embodiment, the device is one of a rheometer and a viscometer.

In an embodiment, the system includes a fluid contained within the measurement cup. The fluid may include particulates.

In an embodiment, the stationary measurement cup includes a stationary particle screen at a bottom of the cup. The stationary measurement cup may also include an integral temperature probe. In an embodiment, the temperature probe is configured to mate with the particle screen.

In yet another embodiment, a system for measuring rheological properties of a material is provided. The system includes a device comprising a stationary measurement cup and an impeller drive head and an impeller attached to the impeller drive head. The impeller includes a shaft comprising first and second pairs of blades and an inverted cone, wherein each of the first pair of blades are oriented substantially vertically, and wherein each of the second pair of blades are oriented at an acute angle with respect to a horizontal plane.

In an embodiment, the device is one of a rheometer and a viscometer.

In an embodiment, the system includes a fluid contained within the measurement cup. The fluid may include particulates.

In an embodiment, the stationary measurement cup includes a stationary particle screen at a bottom of the cup. The stationary measurement cup may also include an integral temperature probe. In an embodiment, the temperature probe is configured to mate with the particle screen.

In still yet another embodiment, a method for measuring rheological properties of a material is provided. The method includes providing a device comprising a stationary cylinder filled with the material and a rotatable sensor drive head, attaching a sensor to the rotatable sensor drive head, inserting the sensor into the stationary cylinder and rotating the sensor. The sensor includes a shaft comprising at least three blades arranged in an interrupted helical shape, and a base configured to receive an end of the shaft.

In an embodiment, the device is one of a rheometer and a viscometer.

In an embodiment, the material is a fluid. The fluid may include particulates.

In an embodiment, the method includes sensing a temperature of the fluid with a temperature probe.

In an embodiment, the method includes placing a stationary particle screen at a bottom of the stationary cylinder. The method may further include mating the temperature probe with the particle screen.

In an embodiment, the method includes rotating the sensor at different angular velocities.

In another embodiment, a method for measuring rheological properties of a material is provided. The method includes providing a device comprising a stationary cylinder filled with the material and a rotatable sensor drive head, attaching a sensor to the rotatable sensor drive head, inserting the sensor into the stationary cylinder, and rotating the sensor. The sensor includes a shaft, at least two curved blades attached to the shaft, each curved blade comprising three sections, and at least two linear blades attached to the shaft.

In an embodiment, the device is one of a rheometer and a viscometer.

In an embodiment, the material is a fluid. The fluid may include particulates.

In an embodiment, the method includes sensing a temperature of the fluid with a temperature probe.

In an embodiment, the method includes placing a stationary particle screen at a bottom of the stationary cylinder. The method may further include mating the temperature probe with the particle screen.

In an embodiment, the method includes rotating the sensor at different angular velocities.

In yet another embodiment, a method for measuring rheological properties of a material is provided. The method includes providing a device comprising a stationary cylinder filled with the material and a rotatable sensor drive head, attaching a sensor to the rotatable sensor drive head, inserting the sensor into the stationary cylinder, and rotating the sensor. The sensor includes a shaft comprising first and second pairs of blades and an inverted cone, wherein each of the first pair of blades are oriented substantially vertically, and wherein each of the second pair of blades are oriented at an acute angle with respect to a horizontal plane.

In an embodiment, the device is one of a rheometer and a viscometer.

In an embodiment, the material is a fluid. The fluid may include particulates.

In an embodiment, the method includes sensing a temperature of the fluid with a temperature probe.

In an embodiment, the method includes placing a stationary particle screen at a bottom of the stationary cylinder. The method may further include mating the temperature probe with the particle screen.

In an embodiment, the method includes rotating the sensor at different angular velocities.

An advantage of the present disclosure is to provide improved mixer sensors.

Another advantage of the present disclosure is to provide mixer sensors that provide rheological measurements that closely simulate actual processing conditions.

Yet another advantage of the present disclosure is to provide mixer sensors that can accurately characterize the rheological properties of fluids having particulates.

Still yet another advantage of the present disclosure is to provide mixer sensors that help to prevent settling of particulates in sample fluids during rheological characterization.

Another advantage of the present disclosure is to provide replaceable mixer sensors that may be attached to different rheometer drive heads.

Yet another advantage of the present disclosure is to provide different mixer sensors that may be attached to the same rheometer drive head.

Still yet another advantage of the present disclosure is to provide mixer sensors that are configured to be used in conditions spanning a wide range of temperatures and a wide range of shear rates.

Additional features and advantages are described herein, and will be apparent from, the following Detailed Description.

DETAILED DESCRIPTION

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

As used herein, "about" is understood to refer to numbers in a range of numerals. Moreover, all numerical ranges herein should be understood to include all integer, whole or fractions, within the range.

Rheology is the study of the flow of matter, primarily in the liquid state but also as soft solids or solids under conditions in which they respond with plastic flow rather than deforming elastically in response to an applied force. The flow of substances cannot generally be characterized by a single value of viscosity, although viscosity measurements at specific temperatures can provide valuable information about a material's properties. Rheological studies are generally performed using rheometers, which impose a specific stress field or deformation to the fluid and monitor the resultant deformation or stress. These instruments may operate in steady flow or oscillatory flow, as well as both shear and extension.

A commonly measured rheological property of a material is it's shear viscosity. Shear viscosity, often referred to as simply viscosity, describes the reaction of a material to applied shear stress. In other words, shear stress is the ratio between "stress" (force per unit area) exerted on the surface of a fluid, in the lateral or horizontal direction, to the change in velocity of the fluid as you move down in the fluid (a "velocity gradient"). Volume viscosity or bulk viscosity, describes the reaction to compression and is essential for characterization of acoustics in fluids.

Viscosity and other complex fluid properties such as, for example, density, solids content, etc., can be useful not only as indicators of chemical or physical changes during manufacturing processes, but are also especially essential to the design and operation of processing equipment. However, viscosity evaluations are not easy to obtain when dealing with non-homogeneous systems such as aqueous suspensions including particles, fibers, bacteria, etc., because they often exhibit non-Newtonian properties. As is known in the art, Newtonian fluids are fluids that exhibit a direct linear relationship between the shear stress ($\tau$) necessary for obtaining movement of the fluid and the effective shear rate ($\dot{\gamma}$). The apparent viscosity of these fluids is not affected by the shear rate ($\dot{\gamma}$) and remains constant. Fluids that do not behave according to these principles are called non-Newtonian fluids, two examples of which include shear-thickening and shear-thinning fluids.

Shear-thickening or shear-thinning fluids can have a linear relationship between $\log(\eta)$ and $(\log(K)+(n-1)\log(\dot{\gamma})$, wherein $\dot{\gamma}$ is the shear rate, $\eta$ is the apparent viscosity, K is the consistency index, and n is the power law index. Those fluids exhibiting such a linear relationship are called power law fluids While Newtonian fluids are also power fluids, non-Newtonian fluids are far more complex since the fluids can behave as a power law fluid in one environment, but not in another.

The apparent viscosity ($\eta$) of non-Newtonian fluids depends on the effective shear rate ($\dot{\gamma}$) when the measurement is taken, and the apparent viscosity ($\eta$) can be calculated using the equation $\log(\eta)=\log(K)+((n-1)*\log(\dot{\gamma})$. Newtonian fluids have a power law index (n) of 1, and the value of the consistency index (K) gives the apparent viscosity ($\eta$), called the dynamic viscosity ($\mu$) for these fluids.

As mentioned above, certain difficulties may arise when attempting to characterize the rheological properties of non-homogeneous, or complex, systems. Such difficulties typically relate to, for example, particle settling, phase separation, destruction of material structures, etc. Example of fluids having particulates that experience such problems include certain types of foods. For example, the viscosity of baby food is particularly imporant when considering that it must be thick enough to stay on a spoon, but not so thick that an infant will experience difficulty in swallowing the food. However, since most baby foods are suspensions (e.g., fruit purees), conventional narrow gap viscometers may be unsuitable for rheological characterization of the baby food because of phase separation and subsequent slip at the walls, or errors caused by particles or particle aggregates in the gap.

Indeed, most commercially available rheometers and their related sensors are designed for homogeneous fluid samples (e.g., fluid samples without particulates). When dealing with fluid samples having particulates, however, the particulates have to be strained, or otherwise removed, prior to measurement of its rheological properties. By straining the particulates out of the fluid sample, the only portion of the sample left for measurement is the fluid portion. Measuring solely the fluid portion of the sample gives a less accurate rheological measurement of the sample and might not mimic actual processing conditions.

Accordingly, rheological measurement data for food samples i) with discrete particulates, ii) at a range of temperatures including very low temperatures to very high temperatures (e.g., at aseptic processing conditions, temperatures above 100° T, etc.), and iii) covering a range of shear rates that are found in typical processing pipelines are required for more precise engineering calculations of rheological data measurements. The mixer sensors of the present disclosure are, therefore, designed to predict the rheological characteristics of multiphase (e.g., non-homogeneous) products in laboratory conditions that closely mimic full-scale production conditions. The skilled artisan will immediately appreciate, however, that the present mixer sensors may also be used to characterize the rhelogical properties of fluids without particles, which may be especially useful in situations where phase separation or settling problems occur.

The ideal geometry sensor for product rheological characterization is obtained used a rotational rheometer having a concentric cylinder system, also known as a Couette. A Couetter viscometer consists of a cylinder rotating inside a stationary cup held in a constant temperature bath. The space between the stationary cup and the inner rotating cylinder is filled with the fluid to be measured. As the inner cylinder rotates with uniform angular velocity ($\Omega$), the fluid between the cylinder and the stationary cup moves at a slower rate than the inner cylinder because of drag forces on the fluid. These drag forces may be measured by the viscometer. Alternatively, the outer cup may rotate while the inner cylinder remains stationary. A Couette displays a well-defined shear rate and allows absolute rheological data to be obtained.

In contrast, it may be difficult obtain absolute rheological data using mixer rheometry due to complex flow patterns. However, mixer rheometry data is a good representative of a fluid's rheological characteristics for a fluid that cannot be determined by concentric cylinders systems having narrow gaps. Such fluids may include, for example, fluids having particulates, which typically suffer from settling problems, slip, phase separation, and time dependency, as mentioned above. Mixer viscometers can often be used when these types of fluids require rheological characterization and conventional rotational viscometers cannot be used.

As described in "Bioprocessing Pipelines: Rheology and Analysis" by Steffe and Daubert (2006), each individual mixer viscometer must be characterized prior to use for rheological characterization. The analysis is typically accomplished using dimensionless numbers and standard fluids having known rheological properties. The methods for characterizing each individual mixer viscometer are known in the art and are disclosed in "Bioprocessing Pipelines." These methods consider that the viscosity ($\mu$) of a Newtonian fluid is:

$$\mu = \frac{M}{Ad^3\Omega} = \frac{k''M}{\Omega}$$

where k" is a constant defined as the mixer coefficient: $k''=A^{-1}d^{-3}$, A is a dimensionless constant, and d is the impeller diameter. Newtonian fluids with a known viscosity are used to determine k", which is a function of the system, torque, angular velocity of the impeller and viscosity.

To evaluate power law fluids in a mixer viscometer, the apparent visocity ($\eta$) is defined as a function of the average shear rate:

$$\eta = K(\dot{\gamma}_a)^{n-1}$$

The average shear rate ($\dot{\gamma}_a$) is a product of the mixer viscometer constant (k') and the angular velocity ($\Omega$). To determine this value, the matching viscosity assumption that the Newtonian viscosity and the apparent viscosity are equal at the same shear rate must be applied. Using this assumption, the average shear rate is found to be:

$$\dot{\gamma}_a = \left(\frac{k''M}{\Omega K}\right)^{\frac{1}{n-1}} = \left(\frac{\eta}{K}\right)^{\frac{1}{n-1}}$$

The mixer coefficient (k") and the mixer viscometer constant (k') can then be found by the following process. First, obtain viscosity data of select Newtonian fluids at selected temperatures using a conventional rotational viscometer. Examples of sample Newtonian fluids may include honey, corn syrup, silicone oil, etc. Next, using the same sample Newtonian fluids, obtain experimental data of torque versus angular velocity in the mixer viscometer. Using the equation $\mu\Omega=k''M$, plot the product of viscosity and angular velocity (y-axis) versus torque (x-axis). Then, determine k" as the slope of the equation.

Next, obtain power law (e.g., non-Newtonian) fluids that can be tested in a conventional viscometer and determine the consistency coefficient (K) and the flow behavior index (n) of these materials at appropriate temperatures. Examples of power law fluids include aqueous solutions of guar gum and methylcellulose.

Using the power law fluids, collect experimental data of torque versus angular velocity in the mixer viscometer. Using this data, k" found previously, and the average shear rate formula set forth above, determine the average shear rate at each angular velocity.

Taking the data set of the average shear rate versus angular velocity previously generated, determine the mixer viscometer constant (k') as the slope of the following equation:

$$\dot{\gamma}_a = k'\Omega$$

The above-described process will provide values for the coefficient constant (k") and the mixer viscometer constant (k') that are unique to each specific geometry combination (e.g., each combination of an impeller (e.g., mixer sensor) and its respective cup) tested. Using this method, therefore, any new impeller utilized with a known cup configuration will require characterization to determine it's own unique values for the coefficient constant (k") and the mixer viscometer constant (k').

Accordingly, the impellers/mixer sensors of the present disclosure may be designed for use with a mixer-type rheometer, which includes a mixer sensor having a complex geometry rotating in a stationary cylindrical cup. While the present mixer sensors are discussed with respect to the use of a mixer-type rheometer, the skilled artisan will appreciate that the mixer sensors are not limited to such a configuration and may be used with any viscometer or rheometer capable of using the mixer sensors of the present disclosure. For example, the mixer sensors of the present disclosure may be used with any Haake rheometer, or similar type rheometers. As with the Couette viscometer descrived above, the space between the mixer sensor and the stationary cup is filled with a fluid to be measured.

Known mixer sensors include impeller driven mixers such as a paddle blender and a ribbon blender. A paddle blender generally has a U-shaped horizontal trough, with the impeller shaft running the length of the trough and a paddle or plow blade attached. The blades of the paddle blender generally operate at a faster speed than the blades of a ribbon blender and can offer very short mixing times. A paddle blender is generally a good option when blending materials of dissimilar size, shape and density and can be used for either batch or continuous processes. In addition, they can be used for low-shear mixing applications such as blending friable or over-sized materials.

Similar to the paddle blender, a ribbon blender has a U-shaped horizontal trough, with an impeller shaft running the length of the trough and a long ribbon blade mounted on the shaft. As the shaft rotates, the ribbon blade aerates the mixture, forming a fluidized bed. The ribbon blade is usually configured so that the powder near the outside of the container is moved in one direction and the powder in the middle of the container is moved in the opposite direction. Ribbon blenders are typically used when blending materials of similar shape, size and bulk density, like powders or granular ingredients.

Paddle and ribbon blenders that are known in the art suffer from certain drawbacks, however. For example, the blenders may not be well-suited for high temperatures used with aseptic processing conditions, or may not be constructed for use with a wide range of shear rates, or for use with fluids having particulates. Therefore, the mixer sensors of the present disclosure are designed to be used with mixer viscometry to determine rheological characteristics of fluids having particulates, in a wide range of temperatures and with a wide range of shear rates. The mixer sensors may be manufactured as one integral piece with a viscometer drive head, or may be constructed to be attached to a viscometer drive head.

The mixer sensors of the present disclosure include custom geometries that allow for more accurate and precise measurements of a material's rheological properties. For example, the mixer sensors of the present disclosure are able to precisely determine the characteristics of a fluid having particulates and flowing through a processing pipleline system. By measuring the rheological characteristics of a fluid having particulates, the measurements more closely mimic actual processing conditions, which is not typical of fluids measured after straining of its particulates. Additionally, the mixer sensors of the present disclosure are able to determine these precise rheological measurements across a much larger temperature range, from very low to very high temperatures. The present mixer sensors are able to determine precise rheological characteristics at aseptic temperatures, and temperatures that are higher than 100° C. Further, the mixer sensors of the present disclosure are able to determine rheological measuresments across a much wide range of shear rates.

With respect to high temperature measurement, the mixer sensors of the present disclosure are able to determine precise rheological measurements across a much larger temperature range when compared to prior art mixer sensors. For example, and in an embodiment, the mixer sensors of the present disclosure may be used for rheological measurements at aseptic temperatures. Additionally, the mixer sensors may be use for rheological measurements at temperatures that are greater than 100° C. In an embodiment, the mixer sensors are manufactured using stainless steel, which allows, at least in part, the mixer sensors to be used at high temperatures. In another embodiment, the mixer sensors are designed to be used specifically with a high temperature rheometer such as, for example, a Haake RS-600.

Experiments may be performed to characterize each mixer sensor to determine its constant values of k' and k" in accordance with the methods described above. The values of k' and k" are geometry specific and are only required to be calculated once for each mixer sensor using established mixer viscometry procedures such as those described above. Once the k' and k" values are determined, the values can be programmed into rheometer software, which will allow direct calculation of the viscosity of any sample tested on the rheometer. In this manner, for example, the mixer sensor and drive head are attached to a controller in the rheometer and the controller may perform all calculations in the corresponding subroutines including the formulas described above.

Figure 1:
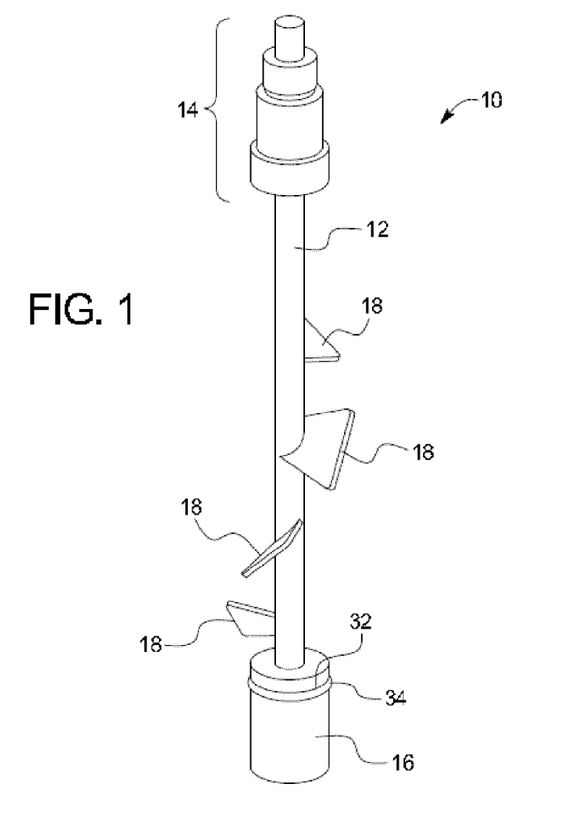
FIG. 1 is a perspective view of a mixer sensor in accordance with an embodiment of the present disclosure.

As shown in FIG. 1, a mixer sensor 10 of the present disclosure includes a shaft 12 attached to a drive head attachment 14 and a base portion 16. Shaft 12 includes a plurality of panels, or blades, 18 that are radially and vertically spaced along shaft 12. Blades 18 are radially spaced about the axis of, and along a circumference of substantially cylindrically shaped shaft 12. Helical mixer sensor 10 is designed to be used with a viscometer or rheometer to determine the rheological properties of fluids, as described above.

Shaft 12 may have a length from about 2 inches to about 6 inches. In an embodiment, shaft 12 has a length of about 4 inches. The entire length of shaft 12, however, may not be visible since a portion of shaft 12 may extend into drive head attachment 14 and/or base portion 16. A visible portion of shaft 12 may be from about 1 to about 5 inches long. In an embodiment, a visible portion of shaft 12 is about 3.5 inches long. A portion of shaft 12 that is not visible to the naked eye when mixer sensor 10 is fully assembled, as shown by FIG. 1, includes a first screw hole that is adjacent a screw hole (not shown) in drive head attachment 14, and a second screw hole that is adjacent a screw hole (not shown) in base portion 16. These screw holes allow shaft 12 to be removeably screwed into drive head attachment 14 and base portion 16, which allows many mixer sensors to be used with the same rheometer/viscometer. In this manner, drive head attachment 14 may be suited for use with a specific rheometer.

Shaft 12 may be manufactured from any material that is strong enough to withstand high torque and high shear rates when in use. Such materials may include, for example, steel, steel alloys, stainless steel, chromium, cobalt-chromium, and other similar metals. Similarly, drive head attachment 14 and base portion 16 may also be manufactured from these, or similar, materials. The skilled artisan will appreciate, however, that mixer sensor 10 is not limited to the use of only these materials and that many materials will have desirable properties for use in this type of application.

Shaft 12 includes a plurality of blades 18 that are spaced apart from each other along shaft 12. The plurality of blades 18 may be radially and/or vertically spaced apart from each other at specific intervals to ensure that any particles in the sample fluid being tested remain suspended. The blades 18 simultaneously rotate and lift the particles of the sample fluid during rotation of shaft 12, before allowing the particles to fall down the cylinder walls of the cylinder in which mixer sensor 10 is rotating. In this manner, mixer sensor 10 promotes movement of any size particle, but large particles in particular (e.g., corn, peas, salsa, tomato sauce, meat sauce, etc.).

As shown in FIG. 1, in an embodiment, adjacent blades 18 may be radially spaced from each other by about 90°. Adjacent blades 18 may also be radially spaced from each other by about 45° to about 135°. Adjacent blades 18 may also be vertically spaced from each other, as measured between a point of intersection of the center of shaft 12 and a first blade 18 and a point of intersection of the center of shaft 12 and a second blade 18. For example, adjacent blades 18 may be spaced apart along shaft 12 from about 0.25 inches to about 1.25 inches. In an embodiment, adjacent blades 18 are spaced apart by about 0.75 inches.

Each of the plurality of blades 18 may be oriented at an angle with respect to horizontal that is the same as or different from any other blade 18 on shaft 12. For example, each of the plurality of blades 18 may be oriented at an angle from about 20° to about 80° with respect to a horizontal plane intersecting a center of each respective blade 18. In an embodiment, each of the plurality of blades 18 may be oriented at an angle of about 45° with respect to a horizontal plane intersecting the center of each respective blade 18, as shown by FIG. 1. In this manner, the plurality of blades 18 of FIG. 1 forms an interrupted helical screw that winds around a portion of shaft 12.

Alternatively, the skilled artisan will appreciate that each of the plurality of blades 18 may be oriented at different angles with respect to a horizontal plane intersecting a center of each respective blade 18. The skilled artisan will also appreciate that the angles need not be formed so that the blades 18 form a front-slash shape, but may be tilted in an opposite direction to form a back-slash shape. As such, the skilled artisan will appreciate that a number of different configurations are possible for the plurality of blades 18 with respect to the angles by which the plurality of blades 18 are offset from horizontal.

As shown in FIG. 1, blades 18 are generally triangularly shaped with a vertex of the triangle being removed. Blades 18 are shaped to conform to the shape of the generally cylindrical shaft 12 where the vertices were removed, and blades 18 may be welded or otherwise attached to shaft 12. In an embodiment where blades 18 are substantially triangular shaped, as shown in FIG. 1, a flat end of blade 18 opposite shaft 12 may have a length that is from about 0.3 inches to about 1 inch. In an embodiment, a flat end of blade 18 opposite shaft 12 has a length of about 0.6 inches. The skilled artisan will appreciate that blades 18 may have any shape and size that is suitable for mixing/suspending particulates in a fluid during rotation of shaft 12.

Drive head attachment 14, as illustrated in the present application, may be configured to mate with a specific rheometer. As such, in an embodiment, drive head attachment 14 may have a magnetic portion that mates with a magnetic portion of the rheometer. In an embodiment, the rheometer is a Haake RS 600. Drive head attachment 14 may have any dimensions necessary to properly mate with the rheometer. Drive head attachment 14 may have a length from about 0.5 to about 2 inches. In an embodiment, drive head attachment 14 has a length of about 1 inch. The skilled artisan will appreciate, however, that drive head attachment 14 may be redesigned to make the mixer sensors of the present disclosure compatible with any other rheometer and/or viscometer. As mentioned previously, shaft 12 may be attached to drive head attachment 14 with screws.

Similarly, and as is also mentioned previously, shaft 12 may be attached to base portion 16 with screws. Base portion 16 may be a substantially cylindrical base that accepts a portion of shaft 12 therein and helps to stabilize shaft 12 during rotation. Base portion 16 may have any height, so long as a top of base portion 16 does not contact a bottom of the lowest blade 18. In this manner, there should be a space between a top surface of base portion 16 and a bottom of the lowest blade 18. Similarly, base portion 16 may have any diameter that allows mixer sensor 10 to record adequate rheological data. In this manner, base portion 16 should have a diameter that is smaller than the cylinder in which mixer sensor 10 rotates. In an embodiment, base portion 16 may have a diameter from about 0.25 to about 0.75 inches. In an embodiment, base portion 16 has a diameter of about 0.5 inches.

Figure 2:
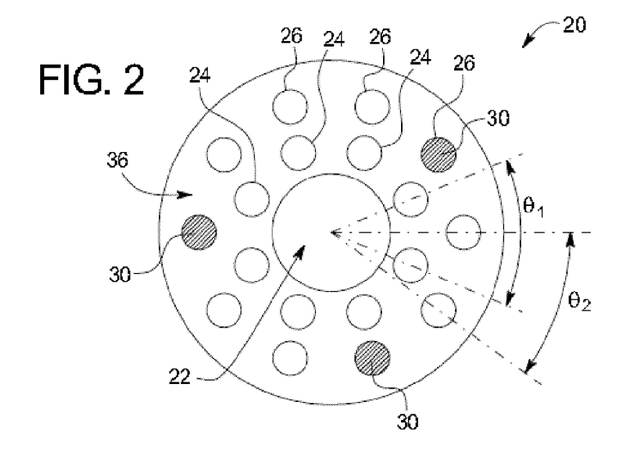
FIG. 2 is a top view of a particle screen in accordance with an embodiment of the present disclosure.

Base portion 16 can be configured to mate with a particle screen 20, as shown in FIG. 2. Particle screen 20 is provided to help prevent particles in the sample fluid from settling during the time in which rheological measurements are taken, as well as to provide easy cleaning of the devices after rheological measurements are taken. In this manner, particle screen 20 may collect particles from the sample fluid that settle out after testing is completed. By removing particle screen 20 from the cylinder in which mixer sensor 10 rotates, much of the mess from the sample fluid can be easily lifted out of the cylinder via particle screen 20 for cleaning.

Particle screen 20 includes a center cutout portion 22 that is configured to mate with base portion 16, and a plurality of inner concentric circles 24 and a plurality of outer concentric circles 26 that are cut out of particle screen 20 to allow some fluid to pass therethrough, but not the particulates suspended in the fluid. Particle screen 20 may have a diameter from about 1 to about 3 inches. In an embodiment, particle screen 20 has a diameter that is about 1.5 inches. Center cutout portion 22 of particle screen 20 may have a diameter that is slightly larger than a diameter of base portion 16. Center cutout portion 22 of particle screen 20 may have a diameter that is from about 0.3 inches to about 0.8 inches. In an embodiment, center cutout portion 22 has a diameter of about 0.55, or 0.6 inches. Inner and outer concentric circles 24, 26 may have a diameter from about 0.1 to about 0.2 inches. In an embodiment, inner and outer concentric circles 24, 26 have a diameter of about 0.15 inches.

Inner concentric circles 24 may be evenly, radially spaced from each other around the center axis of particle screen 20. Additionally, inner concentric circles 24 may be radially spaced apart to form any angle θ therebetween. For example, as shown in FIG. 2, a line drawn from the center axis of particle screen 20 through the center of an inner concentric circle 24 forms an angle $\theta_1$ with a line drawn from the center axis of particle screen 20 through the center of an adjacent inner concentric circle 24. Similarly, outer concentric circles 26 may be evenly, radially spaced from each other around the center axis of particle screen 20. Additionally, outer concentric circles 26 may be radially spaced apart to form any angle θ therebetween. For example, as shown in FIG. 2, a line drawn from the center axis of particle screen 20 through the center of an outer concentric circle 26 forms an angle $\theta_2$ with a line drawn from the center axis of particle screen 20 through the center of an adjacent outer concentric circle 26.

Center cutout portion 22 of particle screen 20 is configured to accept base portion 16 such that a diameter of center cutout portion 22 is slightly larger than a diameter of base portion 16. In this manner, particle screen 20 may be placed inside the cylinder of the rheometer in which mixer sensor 10 rotates, but particle screen 20 does not rotate with mixer sensor 10. In other words, particle screen 20 sits static at the bottom of the cylinder in which mixer sensor 10 rotates, while base portion 16 rotates with shaft 12.

Figure 3:
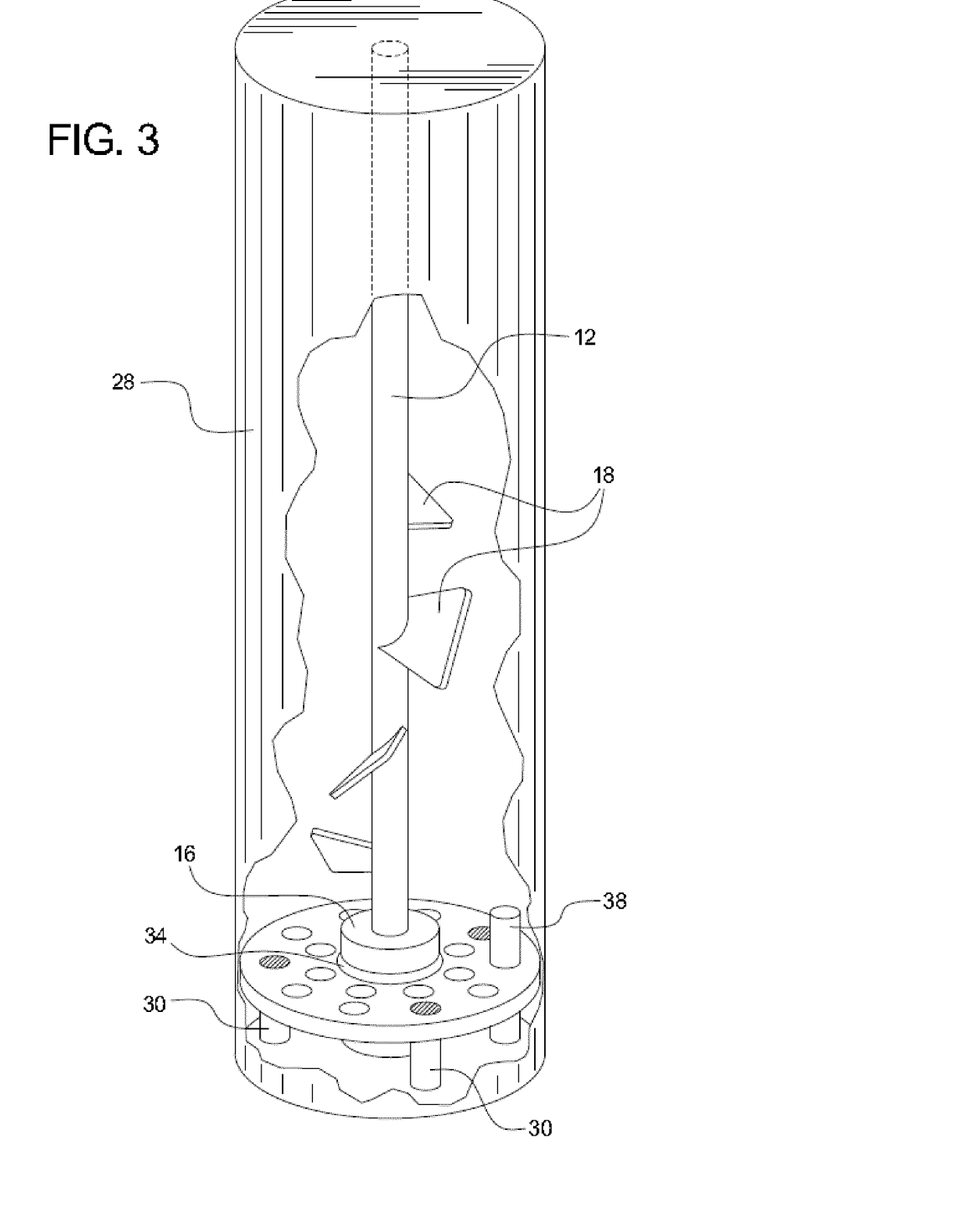
FIG. 3 is a perspective view of a mixer sensor and a particle screen in accordance with an embodiment of the present disclosure.

Particle screen 20 may sit at the bottom of a cylinder 28 in which mixer sensor 10 rotates on a plurality of pegs 30 having equal heights, as shown in FIG. 3. Particle screen 20 may include any number of pegs 30. In an embodiment, particle screen 20 includes from about 2 to about 4 pegs 30. In an embodiment, particle screen 20 includes 3 pegs 30.

Pegs 30 may be formed integrally with particle screen 20 or may be friction fit into any of the plurality of inner, cutout concentric circles 24, or any of the plurality of outer, cutout concentric circles 26. As shown in FIG. 2, pegs 30 may be friction fit into the plurality of outer, cutout concentric circles 26.

Pegs 30 should not extend through a top surface of particle screen 20 so as to contact any portion of blades 18 before or during rotation. This type of contact could cause severe damage to mixer sensor 10 and/or the rheometer that it is attached to as mixer sensor 10 begins to rotate. Additionally, pegs 30 should not have a height that would raise particle screen 20 to a height that is higher than base portion 16. Again, if any portion of particle screen 20 were to contact any part of blades 18 when mixer sensor 10 is rotating, such contact could cause severe damage to either or both of mixer sensor 10 and its attached rheometer.

To prevent any type of destructive contact between particle screen 20 and blades 18, base portion 16 may include any number of o-ring grooves 32 that are constructed and arranged to mate with an o-ring 34 that contacts a top surface 36 of particle screen 20. For example, in FIG. 3, base portion 16 includes one o-ring groove 32 that traverses the circumference of base portion 16 and includes one o-ring 34 that sits in o-ring groove 32. Because o-ring 34 sits on top surface 36 of particle screen 20 when constructed for use, o-ring 34 prevents particle screen 20 from rising upward due to high shear rates during rotation of mixer sensor 10. The skilled artisan will appreciate that o-ring grooves 32 may be located at any place on base portion 16, depending on the desired height of particle screen 20. Similarly, the desired height of particle screen 20 may depend on the size of the particles in the fluid to be measured. As such, base portion 16 may be manufactured with at least two different height locations for o-ring grooves 32 and o-rings 34 to be placed to allow for the use of at least two different particle screens 20 having two different heights.

As has been described above, it should be clear to the skilled artisan that particle screen 20 provides the advantages of avoiding particulate sedimentation and providing the ability to change the mixer sensor to accommodate different product samples with different particle sizes without changing the top and bottom rotor of the mixer sensor.

FIG. 3 also illustrates a temperature probe 38 that may be used to monitor the temperature of a sample fluid being tested. In an embodiment, temperature probe 38 is formed integral with cylinder 28 in which mixer sensor 10 rotates. Accordingly, particle screen 20 may be specifically designed to provide a cutout portion to accept temperature probe 38 therein. Again, temperature probe 38 should not be tall enough to contact a bottom portion of a lowest blade 18 so as to cause damage to mixer sensor 10 when it rotates.

Figure 4:
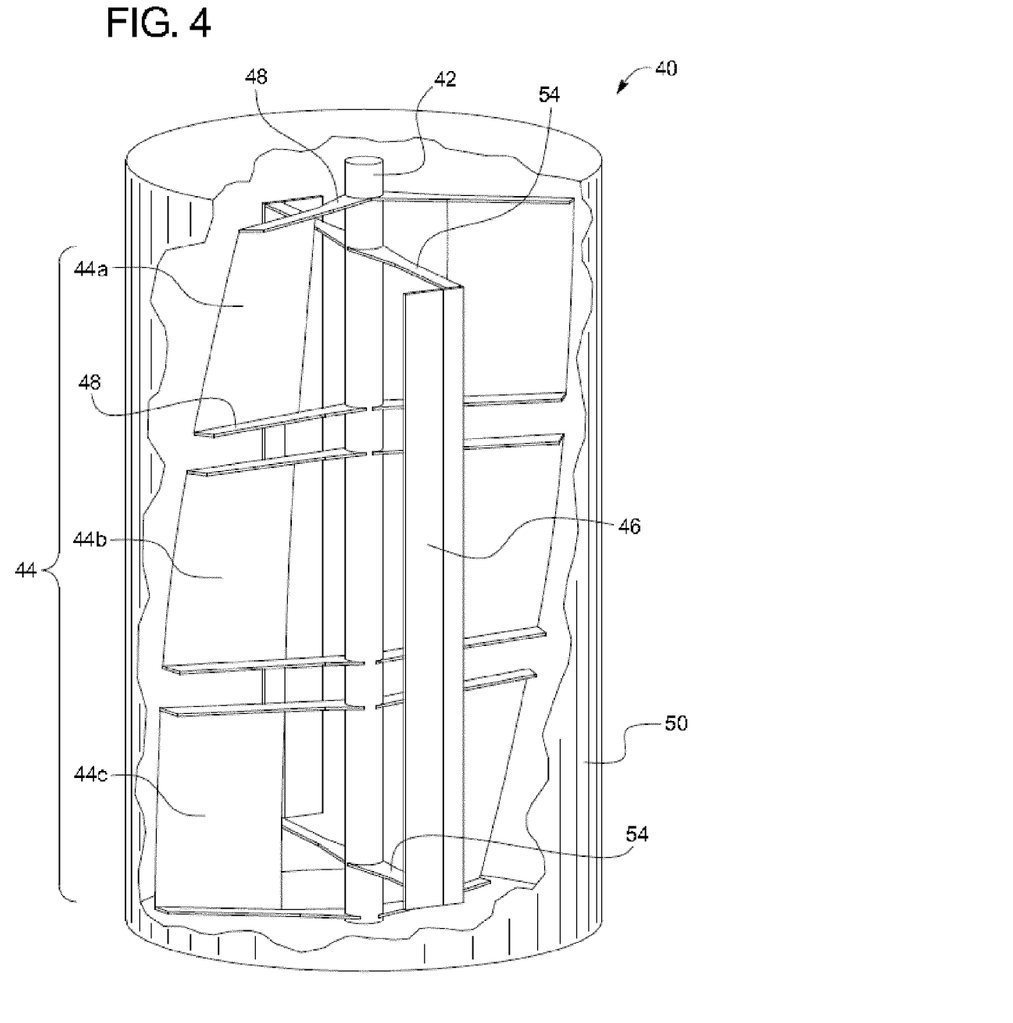
FIG. 4 is a perspective view of a mixer sensor in accordance with an embodiment of the present disclosure.

FIG. 4 illustrates another type of mixer sensor 40 of the present disclosure in a cylinder 50, which includes a shaft 42 connected to at least one curved blade 44 and at least one linear blade 46. Linear blade 46 may be a surface scraper blade. Mixer sensor 40 is designed to be used with a viscometer or rheometer to determine the rheological properties of fluids, as described above. Mixer sensor 40 may be used to promote movement of any size particle, but also long particles in particular (e.g., carrot gratings, green beans, etc.).

Shaft 42 may have a length from about 2 inches to about 6 inches. In an embodiment, shaft 42 has a length of about 4 inches. The entire length of shaft 42, however, may not be visible since a portion of shaft 42 may extend into a drive head attachment (not shown) and/or base portion (not shown), as with mixer sensor 10. Also similar to mixer sensor 10, shaft 42 may include a first screw hole that is adjacent a screw hole (not shown) in a drive head attachment, and a second screw hole that is adjacent a screw hole (not shown) in a base portion. These screw holes allow shaft 42 to be removeably screwed into a drive head attachment and base portion, which allows many mixer sensors to be used with the same rheometer/viscometer. Although a drive head attachment and a base portion are not illustrated in FIG. 4, the skilled artisan will appreciate that both may be used with mixer sensor 40.

Shaft 42 may be manufactured from any material that is strong enough to withstand high torque and high shear rates in use. Such materials may include, for example, steel, steel alloys, stainless steel, chromium, cobalt-chromium, and other similar metals. Similarly, a drive head attachment and a base portion may also be manufactured from these materials. The skilled artisan will appreciate, however, that mixer sensor 40 is not limited to the use of only these materials and that many materials will have desirable properties for use in this type of application.

Figure 5:
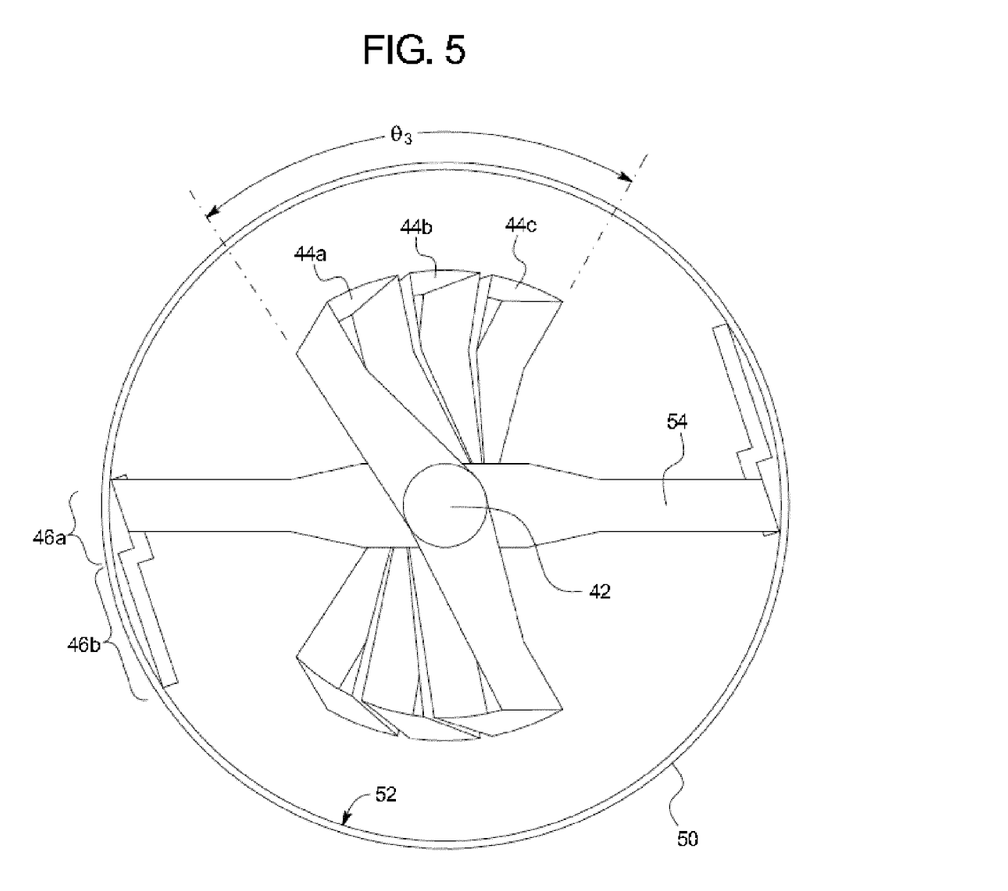
FIG. 5 is a top view of the mixer sensor of FIG. 4 in accordance with an embodiment of the present disclosure.

FIGS. 4 and 5 illustrate mixer sensor 40 including two curved blades 44 and two linear blades 46. However, the skilled artisan will appreciate that mixer sensor 40 may have more or less of each type of blade. As is shown by FIG. 4, curved blades 44 are divided vertically into three sections 44a, 44b, 44c with a small space between each section. Each section 44a, 44b, 44c of curved blades 44 are attached to shaft 42 by at least one substantially horizontal bar 48. Horizontal bars 48 should be configured to withstand high torque values, high shear rates, high stresses, etc., and may be from about 0.25 to about 0.75 inches long from shaft 42 to curved blade 44. In an embodiment, horizontal bars 48 are about 0.5 inches long from shaft 42 to curved blade 44.

Curved blades 44 may have a total length from about 1 inch to about 4 inches. In an embodiment, curved blades 44 have a total length of about 2.7 inches. Each section 44a, 44b, 44c of curved blade 44 may have the same length or a different length. For example, in an embodiment, each of sections 44a, 44b, 44c may have a length of about 0.76 inches with a space between sections 44a, 44b, 44c of about 0.2 inches. Providing curved blades 44 that are broken into several individual sections provides for improved rheological characterization and helps to keep particulates within the sample fluid from settling to the bottom of cylinder 50 in which mixer sensor 40 rotates.

As is shown by FIGS. 4-5, curved blades 44 curve around a portion of shaft 42 to form a ribbon-like shape. Each curved blade 44 may occupy an angular space $\theta_3$ from about 30° to about 80°, as is shown by FIG. 5. In an embodiment, each curved blade 44 occupies an angular space $\theta_3$ that is about 75°.

Unlike curved blades 44, linear blades 46 are not curved around a portion of shaft 42 and are substantially vertical blades having a constant width along the length of the blade. Linear blades 46 should have a constant shape along the length of the blade because linear blades 46 are used to not only help with mixing and rheological characterization, but also may be used to prevent particles from the sample fluid from building up on an inner wall 52 of cylinder 50. In this manner, substantially the entire length and width of linear blades 46 are located substantially adjacent the inner wall 52 of cylinder 50 to scrape any matter from inner wall 52 as mixer sensor 40 rotates in cylinder 50.

Because linear blades 46 are so close to inner wall 52 and may be exposed to built-up matter on same, linear blades 46 should be connected to shaft 42 by at least one rigid and strong horizontal bar 54. In an embodiment, linear blades 46 are connected to shaft 42 by a first horizontal bar 54 at a top portion of the linear blade 46 and a second horizontal bar 54 at a bottom portion of the linear blade 46. Horizontal bars 54 may have a width from about 0.05 inches to about 0.2 inches. In an embodiment, horizontal bars 54 have a width that is about 0.1 inches. To further strengthen horizontal bars 54, the width of the bars 54 may increase gradually moving from an outer portion of the horizontal bar 54 to an inner portion of horizontal bar 54 where it attaches to shaft 42. This increased width may total from about 0.1 inch to about 0.3 inches. In an embodiment, the increased width is about 0.2 inches.

In order to be close enough to scrape the surface of inner wall 52 of cylinder 50, horizontal bars 54 must extend in opposite directions from shaft 42 by a length that is slightly shorter than a radius of cylinder 50 in which mixer sensor 40 rotates. Alternatively, horizontal bar 54 may be one, integral bar that extends across substantially the entire diameter of cylinder 50. In this configuration, horizontal bar 54 may have a linear blade 46 on each end of horizontal bar 54. Further, since cylinder 50 may have a diameter from about 1.0 to about 2.0 inches, horizontal bar 54 should have total length that is slightly less than the diameter of cylinder 50. In an embodiment, cylinder 50 has a diameter of about 1.5 inches. Accordingly, in an embodiment, horizontal bar 54 includes a diameter from about 1.45 to about 1.49 inches. Of course, in an embodiment wherein linear blades 46 are attached to individual horizontal bars 54 that are each attached to shaft 42, horizontal bars 54 with have a length that is slightly less than a radius of cylinder 50, as previously mentioned.

Linear blades 46 may have a length that is shorter than curved blades 44. For example, linear blades 46 may have a length from about 1.5 inches to about 3.5 inches. In an embodiment, linear blades 46 have a length that is about 2.3 inches. FIG. 5 further illustrates that linear blades 46 may be designed to include a first portion 46a that is attached to horizontal bar 54, and a second portion 46b attached to, or integrally formed with, first portion 46a. In this manner, linear blades 46 may have a step-like shape that allows a larger area of linear blades 46 to rotate adjacent to inner wall 52 of cylinder 50 for improved surface scraping. First portion 46a may have a length from about 0.1 to about 0.2 inches. In an embodiment, first portion 46a has a length of about 0.15 inches. Second portion 46b may have a length from about 0.2 inches to about 0.6 inches. In an embodiment, second portion 46b has a length of about 0.4 inches.

As shown in FIG. 5, curved blades 44 may be substantially opposite each other such that a first curved blade 44 is separated from a second curved blade 44 by about 180°. Additionally, curved blades 44 may both be oriented in the same direction in the direction of rotation. In other words, a top section 44a of a first curved blade 44 may pass a set reference point before a bottom section 44c of the first curved blade 44. Similarly, a top section 44a of a second curved blade 44 (that is opposite the first curved blade 44) may pass a set reference point before a bottom section 44c of the second curved blade 44. In this manner, first and second curved blades 44 may have similar shapes and may be oriented in similar directions.

Similarly, linear blades 46 may be substantially opposite each other such that a first linear blade 46 is separated from a second linear blade 46 by about 180°. Additionally, linear blades 46 may both be oriented in the same direction in the direction of rotation. In other words, and as shown in FIG. 5, linear blades 46 may be attached to horizontal bar 54 in opposite directions such that first portions 46a rotate ahead of second portions 46b. In this manner, first and second linear blades 46 may have similar shapes and may be oriented in similar directions.

Figure 6:
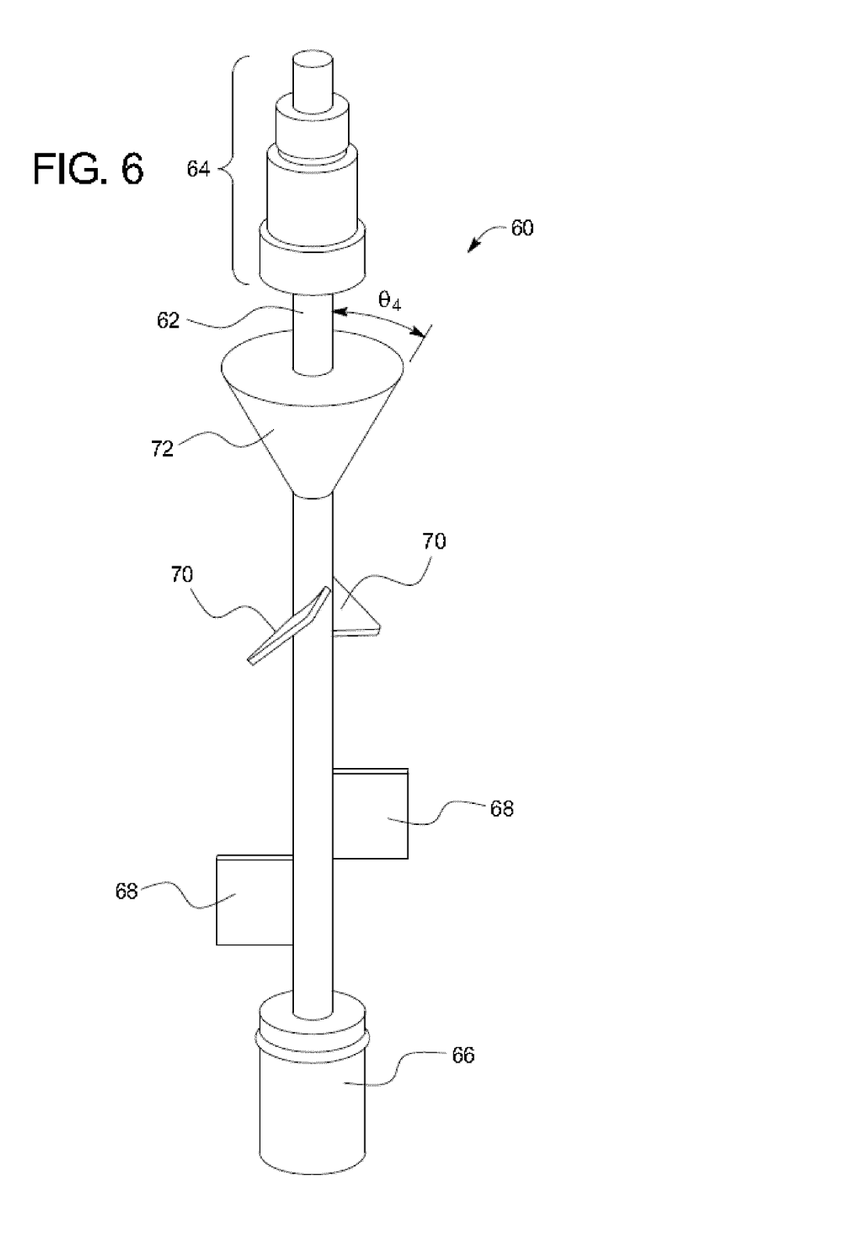
FIG. 6 is a perspective view of a mixer sensor in accordance with an embodiment of the present disclosure.

As shown in FIG. 6, another mixer sensor 60 of the present disclosure includes a shaft 62 attached to a drive head attachment 64 and a base portion 66, similar to mixer sensor 10. Shaft 62 includes a first set of blades 68, a second set of blades 70, and a solid cone 72. Each set of blades 68, 70, may be radially and vertically spaced along shaft 62. As with the previously described mixer sensors, mixer sensor 60 is designed to be used with a viscometer or rheometer to determine the rheological properties of fluids, as described above.

Shaft 62 may have a length from about 2 inches to about 6 inches. In an embodiment, shaft 62 has a length of about 4 inches. The entire length of shaft 62, however, may not be visible since a portion of shaft 62 may extend into drive head attachment 64 and/or base portion 66. A visible portion of shaft 62 may be from about 1 to about 5 inches long. In an embodiment, a visible portion of shaft 62 is about 3.5 inches long. A portion of shaft 62 that is not visible to the naked eye when mixer sensor 60 is fully assembled, as shown by FIG. 6, includes a first screw hole that is adjacent a screw hole (not shown) in drive head attachment 64, and a second screw hole that is adjacent a screw hole (not shown) in base portion 66. These screw holes allow shaft 62 to be removeably screwed into drive head attachment 64 and base portion 66, which allows many mixer sensors to be used with the same rheometer/viscometer. In this manner, since drive head attachment 64 is manufactured to mate with, for example, a specific rheometer, drive head attachment 64 may be attached to several different types of mixer sensors to provide flexibility of measurement for the rheometer.

Shaft 62 may be manufactured from any material that is strong enough to withstand high torque and high shear rates in use. Such materials may include, for example, steel, steel alloys, stainless steel, chromium, cobalt-chromium, and other similar metals. Similarly, drive head attachment 64 and base portion 66 may also be manufactured from these materials. The skilled artisan will appreciate, however, that mixer sensor 60 is not limited to the use of only these materials and that many materials will have desirable properties for use in this type of application.

Shaft 62 includes a plurality of blades 68, 70 that are spaced apart from each other along shaft 62. The plurality of blades 68, 70 may be radially and/or vertically spaced apart from each other at specific intervals to ensure that any particles in the sample fluid being tested remain suspended therein. The blades 68, 70 simultaneously rotate and lift the particles of the sample fluid during rotation of shaft 62, before allowing the particles to fall down the cylinder walls of the cylinder (not shown) in which mixer sensor 60 is rotating. In this manner, mixer sensor 60 promotes movement of any size particle, but is specifically beneficial for characterizing starch-based sample fluids.

As shown in FIG. 6, a first pair of blades 68 may be located toward the bottom of shaft 62, allowing a small space between a top surface of bottom portion 66 and a bottom-most portion of the lowest blade 68. The space may be from about 1 to 2 mm, or about 1.5 mm. First pair of blades 68 may be separated from each other by about 180° about a center axis of shaft 62 and along the circumference of shaft 62, and may be at the same horizontal height, or may be at different horizontal heights. As shown in FIG. 6, blade 68 on the left side of shaft 62 is lower than blade 68 on the right side of shaft 62. In an embodiment, a bottom of blade 68 on the right side of shaft 62 is at the same height as a top of blade 68 on the left side of shaft 62.

Each of the first pair of blades 68 may have the same or different dimensions. For example, each of first pair of blades 68 may have a width from about 10 to 15 mm and a height from about 10 to 20 mm. In an embodiment, each of first pair of blades 68 has a width of about 13 mm and a height of about 15 mm. The width of each of first pair of blades 68 should leave a space between blades 68 and an inner wall of the cylinder in which mixer sensor 60 rotates.

The space between blades 68 and the cylinder should be at least about 4 to 5 mm, or about 4.5 mm.

As is also shown in FIG. 6, a second pair of blades 70 may be located toward a middle of shaft 62 and above first pair of blades 68. Shaft 62 should have an area, or space, between first set of blades 68 and second set of blades 70 that does not have any blades located thereon. The length of the space between first set of blades 68 and second set of blades 70 may be from about 5 mm to about 15 mm. In an embodiment, the length of the space between first set of blades 68 and second set of blades 70 is about 10 mm.

Second pair of blades 70 may be separated from each other by about 180° about a center axis of shaft 62 and along the circumference of shaft 62, and may be at the same height, or may be at different heights. As shown in FIG. 6, blade 70 on the front side of shaft 62 is at the same height as blade 70 on the back side of shaft 62. In other words, while blades 68 are illustrated as being in the same plane as the paper, blades 70 are extending into and out of the paper in a plane that is perpendicular with the paper. As is also clearly illustrated in FIG. 6, each of second pair of blades 70 is rotated slightly from vertical in a counter-clockwise direction. For example, each of second pair of blades 70 may be rotated from about 5° to about 45° from vertical in a counter-clockwise direction. In an embodiment, each of second pair of blades 70 may be rotated from about 10° to about 30° from vertical in a counter-clockwise direction. In an embodiment, each of second pair of blades 70 may be rotated about 15° from vertical in a counter-clockwise direction. Blades 70 may also be rotated from vertical in a clockwise direction.

Prior to rotation of each of second pair of blades 70, however, blades 70 may have a height from about 10 to about 20 mm. In an embodiment, each of second pair of blades 70 has a height from a bottom side to a top side of about 15 mm. Each of second pair of blades 70 may also have a width from about 10 mm to about 15 mm. In an embodiment, each of second pair of blades 70 may have a width of about 13.5 mm.

At a top portion of shaft 62, mixer sensor 60 includes an inverted cone 72. Cone 72 is designed to help keep any particles present in the sample fluid suspended in the sample fluid, and to prevent them from settling on a particle screen (not shown) used with mixer sensor 60, or the floor of the cylinder (not shown) in which mixer sensor 60 rotates. Since cone 72 is inverted, the base of cone 72 is located at a higher location on shaft 62 than the apex of cone 72, which has been lopped off, making cone 72 frustoconical in shape. For ease of description, however the conical frustum on shaft 62 will be described as cone 72.

The base of cone 72 may have any diameter that fits within the cylinder in which mixer sensor 60 rotates. For example, the base of cone 72 may have a diameter from about 20 mm to about 40 mm. In an embodiment, the base of cone 72 may have a diameter of about 30 mm. Additionally, measuring from the apex, cone 72 forms and angle $\theta_4$ with shaft 62 and the lateral surfaces of cone 72, as shown by FIG. 6. $\theta_4$ may be from about 15° to about 45°. In an embodiment, $\theta_4$ may be about 30° or 31°. Similar to the space on shaft 62 between blades 68 and blades 70, there may be a space on shaft 62 between a top-most portion of blades 70 and a bottom-most portion of inverted cone 72. The length of this space along shaft 62 may be from about 5 mm to about 15 mm. In an embodiment, the length of this space along shaft 62 may be about 10 mm. Although not illustrated in FIG. 6, mixer sensor 60 may be used in a cylinder along with a particle screen similar to particle screen 20 described above.

Methods

Systems and methods for using the mixer sensors of the present disclosure are also provide. For example, the present disclosure provides systems for measuring rheological properties of a material. The system includes a device comprising a stationary measurement cup and an impeller drive head and an impeller attached to the impeller drive head. The impeller includes a shaft comprising at least three blades arranged in an interrupted helical shape and a base configured to receive an end of the shaft.

Another system for measuring rheological properties of a material is also provided. The system includes a device comprising a stationary measurement cup and an impeller drive head, and an impeller attached to the impeller drive head. The impeller includes a shaft, at least two curved blades attached to the shaft, each curved blade comprising three sections, and at least two linear blades attached to the shaft.

Yet another system for measuring rheological properties of a material includes a device comprising a stationary measurement cup and an impeller drive head and an impeller attached to the impeller drive head. The impeller includes a shaft comprising first and second pairs of blades and an inverted cone, wherein each of the first pair of blades are oriented substantially vertically, and wherein each of the second pair of blades are oriented at an acute angle with respect to a horizontal plane.

Method for measuring rheological properties of a material are also provided. One example of a method includes providing a device comprising a stationary cylinder filled with the material and a rotatable sensor drive head, attaching a sensor to the rotatable sensor drive head, inserting the sensor into the stationary cylinder and rotating the sensor. The sensor includes a shaft comprising at least three blades arranged in an interrupted helical shape, and a base configured to receive an end of the shaft.

Another example of a method for measuring rheological properties of a material includes providing a device comprising a stationary cylinder filled with the material and a rotatable sensor drive head, attaching a sensor to the rotatable sensor drive head, inserting the sensor into the stationary cylinder, and rotating the sensor. The sensor includes a shaft, at least two curved blades attached to the shaft, each curved blade comprising three sections, and at least two linear blades attached to the shaft.

Yet another method for measuring rheological properties of a material includes providing a device comprising a stationary cylinder filled with the material and a rotatable sensor drive head, attaching a sensor to the rotatable sensor drive head, inserting the sensor into the stationary cylinder, and rotating the sensor. The sensor includes a shaft comprising first and second pairs of blades and an inverted cone, wherein each of the first pair of blades are oriented substantially vertically, and wherein each of the second pair of blades are oriented at an acute angle with respect to a horizontal plane.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An apparatus for measuring rheological properties of a material, the apparatus comprising:
    a drive head attachment so constructed and arranged to attach to one of a rheometer and a viscometer;
    a shaft comprising at least three blades, wherein the plurality of blades are radially spaced about an axis of the shaft, wherein the drive head attachment is configured to receive a top end of the shaft therein, wherein each of the plurality of blades is rotated about 20° to about 80° from horizontal, and wherein the plurality of blades are vertically spaced from each other by about 0.25 inches to about 1.25 inches; and
    a base configured to receive an end of the shaft, and wherein the base further comprising at least one o-ring groove configured to accept an o-ring seal and wherein the base is configured to receive a bottom end of the shaft.

2. The apparatus according to claim 1, wherein at least one of the shaft, the base, the drive head attachment, is manufactured from a material selected from the group consisting of steel, steel alloys, stainless steel, chromium, cobalt-chromium, and combinations thereof.

3. The apparatus according to claim 2, wherein the material is cobalt-chromium.

4. The apparatus according to claim 1, wherein the plurality of blades are arranged in an interrupted helical shape, and radially spaced from each other by about 45° to about 135°.

5. The apparatus according to claim 1, wherein each of the plurality of blades is substantially triangularly shaped.

6. The apparatus according to claim 1, wherein the base is further configured to mate with a particle screen, wherein the particle screen comprises an open center portion that is configured to receive the base, and wherein the particle screen comprises a diameter from about 1 to about 3 inches.

7. The apparatus according to claim 6, wherein the particle screen is substantially circular in shape and further comprises a plurality of holes between the center portion and the circumference.

8. The apparatus according to any one of claim 6, wherein the particle screen rests on a plurality of pegs that are formed integrally with particle screen or are friction fit into the holes of particle screen.

9. The apparatus according to claim 6, further comprising a temperature probe, wherein the temperature probe is configured to extend through at least one of the holes of the particle screen.

10. The apparatus according to claim 1, wherein at least three blades is:
    at least two curved blades attached to the shaft, each curved blade comprising three sections; and
    at least two linear blades attached to the shaft.

11. The apparatus according to claim 10, wherein each of the three sections are separated by a space.

12. The apparatus according to claim 10, wherein each of the three sections are equal in length.

13. The apparatus according to claim 10, wherein the linear blades are surface scraper blades.

14. The apparatus according to claim 10, wherein each of the linear blades is attached to the shaft at a top end and a bottom end of the linear blade.

15. The apparatus according to claim 10, wherein each of the linear blades has a length from about 1.5 inches to about 3.5 inches.

16. The apparatus according to claim 10, wherein each of the linear blades comprises a step-shape forming two different parallel portions of the linear blade, wherein the first parallel portion of the linear blade has a length from about 0.1 to about 0.2 inches and wherein the second parallel portion of the linear blade has a length from about 0.2 inches to about 0.6 inches.

17. The apparatus according to claim 1, wherein:
    the shaft comprising at least three blades comprises a first and second pairs of blades and an inverted cone, wherein each of the first pair of blades are oriented substantially vertically, wherein each of the second pair of blades are oriented at an acute angle with respect to a horizontal plane, wherein each of the first pair of blades has a width from about 10 to 15 mm, and wherein the cone forms an angle with the shaft from about 15° to about 45°.

18. The apparatus according to claim 17, wherein the first pair of blades and the second pair of blades are each radially spaced about an axis of the shaft.

19. The apparatus according to claim 17, wherein the first pair of blades and the second pair of blades are each radially spaced from each other by about 180°.

20. The apparatus according to claim 17, wherein the first pair of blades are vertically spaced from each other such that a bottom side of a first blade is at the same vertical height as a top side of a second blade.

21. The apparatus according to claim 17, wherein the first pair of blades and the second pair of blades are individually comprise a shape selected from the group consisting of rectangle, square, and combinations thereof.

22. The apparatus according to claim 17, wherein the first pair of blades are located at a bottom portion of the shaft.

23. The apparatus according to claim 17, wherein the second pair of blades are located in substantially the same horizontal plane.

24. The apparatus according to claim 17, wherein the inverted cone is located at a top portion of the shaft.

25. A system for measuring rheological properties of a material, the system comprising:
    a device comprising a stationary measurement cylinder and a rotatable sensor drive head; and
    a sensor attached to the rotatable sensor drive head, the sensor comprising:
        a shaft comprising at least three blades arranged in an interrupted helical shape; and
        a base configured to receive an end of the shaft, wherein the device is one of a rheometer and a viscometer.

26. The system according to claim 25, further comprising a fluid contained within the stationary measurement cylinder.

27. The system according to claim 26, wherein the fluid comprises particulates.

28. The system according to claim 25, wherein the stationary measurement cylinder comprises a stationary particle screen at a bottom of the cylinder.

29. The system according to claim 25, wherein the stationary measurement cylinder comprises an integral temperature probe.

30. The system according to claim 25, wherein the at least three blades is at least two curved blades attached to the shaft, each curved blade comprising three sections, and at least two linear blades attached to the shaft.

31. The system according to claim 25, wherein the shaft comprising at least three blades is a shaft comprising first and second pairs of blades and an inverted cone, wherein each of the first pair of blades are oriented substantially vertically, and wherein each of the second pair of blades are oriented at an acute angle with respect to a horizontal plane.

32. A method for measuring rheological properties of a material, the method comprising the steps of:
providing a device comprising a stationary cylinder filled with the material and a rotatable sensor drive head;
attaching a sensor to the rotatable sensor drive head, the sensor comprising a shaft comprising at least three blades arranged in an interrupted helical shape, and
a base configured to receive an end of the shaft;
inserting the sensor into the stationary cylinder; and
rotating the sensor, wherein the device is one of a rheometer and a viscometer.

33. The method according to claim 32, wherein the material is a fluid.

34. The method according to claim 32, wherein the fluid comprises particulates.

35. The method according to claim 32, further comprising sensing a temperature of the fluid with a temperature probe.

36. The method according to claim 32, further comprising placing a stationary particle screen at a bottom of the stationary cylinder.

37. The method according to claim 32, wherein the at least three blades is at least two curved blades attached to the shaft, each curved blade comprising three sections, and
at least two linear blades attached to the shaft;
inserting the sensor into the stationary cylinder; and
rotating the sensor.

38. The method according to claim 37, further comprising rotating the sensor at different angular velocities.

39. The method according to claim 32, wherein the shaft comprising at least three blades is a shaft comprising first and second pairs of blades and an inverted cone, wherein each of the first pair of blades are oriented substantially vertically, and wherein each of the second pair of blades are oriented at an acute angle with respect to a horizontal plane;
inserting the sensor into the stationary cylinder; and
rotating the sensor.

40. The method according to claim 32, further comprising rotating the sensor at different angular velocities.

* * * * *